US006790962B2

(12) United States Patent
Rotenberg et al.

(10) Patent No.: US 6,790,962 B2
(45) Date of Patent: Sep. 14, 2004

(54) DEQUALINIUM ANALOGS

(75) Inventors: Susan A. Rotenberg, Bayside, NY (US); A. David Baker, Melville, NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

(21) Appl. No.: 10/328,693

(22) Filed: Dec. 24, 2002

(65) Prior Publication Data

US 2003/0118529 A1 Jun. 26, 2003

Related U.S. Application Data

(62) Division of application No. 09/953,074, filed on Sep. 14, 2001, now abandoned.
(60) Provisional application No. 60/232,970, filed on Sep. 14, 2000.

(51) Int. Cl.$^7$ .................. C07D 215/16; C07D 215/38
(52) U.S. Cl. .................. 546/167; 546/153; 546/159
(58) Field of Search .................. 546/153, 159, 546/167

(56) References Cited

U.S. PATENT DOCUMENTS

| 5,208,011 A | 5/1993 | Vaughan |
| 5,914,102 A | 6/1999 | Fowler et al. |
| 6,090,619 A | 7/2000 | Weissig et al. |
| 6,171,863 B1 | 1/2001 | Weissig et al. |
| 2001/0001067 A1 | 5/2001 | Weissig et al. |

OTHER PUBLICATIONS

Galanakis, J. Med. Chem, vol 39, pp 3592–3595, 1996.*
Qin, J Med Chem, vol 43, pp 1413–1417, 2000.*
Medline abstract 1999402168, abstract of Lancet, vol 354 (9180), pp 723–729, 1999.*
Qin, et al.; "Inhibition of Protein Kinase Cα by Dequalinium Analogues: Dependence on Linker Length and Geometry," Journal of Medicinal Chemistry, vol. 43, No. 7, pp. 1413–1417; (2000).
Sullivan, et al.; "Photo–Induced Inactivation of Protein Kinase Cα by Dequalinium Inhibits Motility of Murine Melanoma Cells," Molecular Pharmacology, vol. 58, No. 4, pp. 729–737; (2000).
Rotenberg, et al.; "Deletion Analysis of Protein Kinase Cα Reveals a Novel Regulatory Segement," J. Biochem., vol. 124, pp. 756–763; (1998).
Galanakis, et al.; "Synthesis and Quantitative Structure–Activity Relationships of Dequalinium Analogues as K+ channel Blockers :Investigation into the Role of the Substituent at Position 4 of the Quinoline Ring," J. Med. Chem. 38: 3536–3546 (1995).
Galanakis, et al.; "Synthesis and Quantitative Structure–Activity Relationships of Dequalinium Analogues as K+ channel Blockers. Investigations on the role of the Charged Heterocycle, " J. Med. Chem. 38: 595–606 (1995).
Galanakis, et al.; "Synthesis and Quantitative Structure–Activity Relationship of a Novel Series of Small Conductance Ca2+– Activated K+ Channel Blockers Related to Dequalinium, " J. Med. Chem. 39: 359–370 (1996).
Galanakis, et al.; "synthesis and Pharmacological Testing of Dequalinium Analogues as Blockers of the Apamin–Sensitive Ca2+–Activated K+ Channel: Variation of the Length of the Alkylene chain, " J. Med. Chem. 39: 3592–3595 (1996).
Rotenberg et al., "Photoinduced Inactivation of Protein Kinase C by Dequalinium Identifies the RACK–1 binding Domain as a recognition Site," *J. Biological Chemistry*, pp. 2390–2395, 273:4, (1995).
Rotenberg et al., "Inhibition of Rodent Kinase C by the Anticarcinoma Agent Dequalinium$^1$," *Cancer Research*, pp. 677–685, 50 (1990).
Cox, "Chemical Structure and Antimicrobial Activity in Two Related Homologous Series of Quaternary Ammonium Compounds," Chem. Phys. Appl. Surface Active Subst., 1: 79–91 (1967) [Abstract].
Cox, et al., "A Series of Decamethylenebis [(4–substituted amino) quinaldinium] Salts with Potent Antibacterial Properties," J. Pharm. Pharmacol. 19:155–60 (1967) [Abstract].

(List continued on next page.)

*Primary Examiner*—D. Margaret Seaman
(74) *Attorney, Agent, or Firm*—Irving N. Feit; Hoffmann & Baron, LLP

(57) ABSTRACT

A composition for protecting human skin from harmful effects of the sun, the composition comprising a topically effective amount of:

(a) a first chemical compound that absorbs ultraviolet light sufficiently to reduce significantly the damage to human skin from harmful effects of ultraviolet light; and
(b) a second chemical compound having the formula:

$$(Q\text{-}L\text{-}Q)_w^{+2} X_y^{-z}$$

wherein:
Q represents 4-E-2-$R_3$-1-quinolinium;
E represents $NR_1R_2$, COO $R_1$, $OR_1$, I, Br, Cl, F, or $NO_3$
N represents a nitrogen atom;
$R_1$ and $R_2$ independently represent hydrogen or lower alkyl;
$R_3$ represents E, hydrogen or lower alkyl;
L represents a chain comprising n atoms, the atoms in the chain being t carbon atoms and 0 to approximately 0.5t heteroatoms;
the minimum value of n is 12;
the maximum value of n is 22;
X represents an anion; and
w represents 1 or 3, y represents 1 or 2 and z represent 1, 2 or 3, with the proviso that 2w=yz.

23 Claims, 5 Drawing Sheets

OTHER PUBLICATIONS

Weissig et al., DQAsomes: Structural Requirements for Vesicle Formation, Proceedings of the International Symposium on Controlled Release of Bioactive Materials, 26:519–520 (1990) [Abstract].

Taylor, et al, "Capillary Electrophoresis and Liquid Chromatography in the Analysis of Some Quaternary Ammonium Sales Used in Lozenges as Antibacterial Agents", Journal of Capillary Electrophoresis, 5:45–50 (1998) [Abstract].

Galanakis et al.; "Abstract: On the Concept of a Bivalent Pharmacophore for SKCa Channel Blockers. Synthesis, Pharmacological Testing, and Radioligand Binding Studies on Mono–, Bis–, and Trisquinolinium Compounds," Dept. Chemistry, U. of College London, Archiv der Pharmazie, 329(12): pp. 524–528 (1996).

* cited by examiner

DEQUALINIUM ANALOGS

This application is a divisional of co-pending U.S. application Ser. No. 09/953,074 filed on Sep. 14, 2001, ABN and claims the benefit of U.S. Provisional Application No. 60/232,970, filed Sep. 14, 2000, which is incorporated herein by reference in its entirety.

The invention described in this specification was supported by a grant from the National Institutes of Health (CA60618). The United States has certain rights in this invention.

BACKGROUND

Dequalinium (C10-DECA) (quinolinium, 1,1'-(1,10-decanediyl) bis (4-amino-2-methyl diiodide) (see 1c in Table 1) was sold for over thirty years as an antimicrobial agent and the active ingredient in mouthwash and other topical formulations. Since 1987, C10-DECA has been studied as a potent antitumor agent that recognizes several isoforms (e.g., $\alpha$, $\beta1$) of protein kinase C (PKC) in vitro (IC50=10–14 $\mu$M) and in cells[1,2]. This monomeric serine/threonine protein kinase consists of a family of eleven structurally-related isoforms and is well-known for its role in cellular signaling pathways that govern normal cell growth and differentiation[3]. Because of its function in tumor formation and metastasis, PKC continues to attract interest as a target for new chemotherapeutic agents.

A potent anti-tumor agent in several animal models[4], C10-DECA is accumulated by transformed cells in culture to a greater extent than by non-transformed cells[5,6]. C10-DECA inhibits PKC activity in vitro and in cells at low micromolar concentrations[1,2] by interfering with binding sites in both the regulatory[1,2] and catalytic domains[2,7]. Inhibition of catalytic activity involves a site or sites located in the catalytic domain of $PKC_\alpha$[2,7], but an additional C10-DECA recognition site in the regulatory domain involving the RACK-1 (Receptor for Activated C-Kinase) binding domain has also been demonstrated[1].

A series of $PKC_\alpha$ mutants that represented progressive truncation from the amino-terminus (regulatory domain) have been tested for sensitivity to inhibition to C10-DECA in order to examine the importance of the regulatory domain to C10-DECA-mediated inhibition of catalytic activity. That analysis revealed that the sites of interaction in the regulatory and catalytic domains are independent of each other, and that the site at which C10-DECA produces inhibition of catalytic activity lies exclusively in the catalytic domain[7]. One of the inventors (SAR) has tested structurally homologous protein kinases for inhibition, and found them to be insensitive to micromolar C10-DECA concentrations. The homologous protein kinases included the cAMP-dependent protein kinase (PKA), the calmodulin-dependent myosin light chain kinase, and the pp60[src] tyrosine protein kinase. The finding that PKA is insensitive to DECA at high micromolar concentrations is compelling in view of the close sequence homology of the PKC and PKA catalytic domains. With respect to these other protein kinases, the key site recognized by C10-DECA is apparently unique to PKC. Additional cellular targets of C10-DECA have been reported, however, namely the mitochondrial F1-ATPase[8], calmodulin-dependent phosphodiesterase[9], and the calcium-activated K[+]-channel[10].

An unusual property of C10-DECA is that it can be photolyzed with longwave UV light, which converts it into an irreversible inhibitor of PKC activity[1]. Photoreactivity was previously employed to demonstrate inactivation of recombinant $PKC_\alpha$ activity in vitro and $PKC_\alpha$ translocation in cells[1].

There is a need, however, to optimize the ability of C10-DECA to inhibit the activity of an isoform of protein kinase C, especially protein kinase C. There is a particular need to optimize the beneficial manifestations of inhibiting the activity of an isoform of protein kinase C, such as inhibiting the motility of pre-cancerous cells, inhibiting the growth of pre-cancerous or malignant cells, and inhibiting the metastasis of malignant cells.

SUMMARY OF THE INVENTION

In one embodiment, the invention relates to a chemical compound having the formula:

  (Formula 1)

or

  (Formula 2)

wherein:
Q represents 4-E-2-$R_3$-1-quinolinium;
E represents $NR_1R_2$, COO $R_1$, $OR_1$, I, Br, Cl, F, or $NO_3$
N represents a nitrogen atom;
$R_1$ and $R_2$ independently represent hydrogen or lower alkyl;
$R_3$ represents E, hydrogen or lower alkyl;
L represents a chain comprising n atoms, the atoms in the chain being t carbon atoms and 0 to approximately 0.5t heteroatoms;
the minimum value of n is 12;
the maximum value of n is 22;
T represents hydrogen or a chain comprising m atoms, the atoms in the chain being t carbon atoms and 0 to approximately 0.5t heteroatoms;
the minimum value of m is 6;
the maximum value of m is 22;
X represents an anion;
w represents 1 or 3, y represents 1 or 2 and z represents 1, 2 or 3, with the proviso that 2w=yz; and
u and v represent 1, 2, or 3 with the proviso that u=v.

In another embodiment, the invention relates to a chemical compound having the formula:

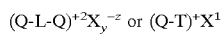

wherein:
Q represents 4-$NR_1R_2$-2-$R_3$-1-quinolinium;
N represents a nitrogen atom;
$R_1$ and $R_2$ independently represent hydrogen or lower alkyl;
$R_3$ represents hydrogen or lower alkyl;
L represents a 1,n-aliphatic chain comprising n carbon atoms;
n represents 12–22;
T represents hydrogen or a 1,m-aliphatic chain comprising m carbon atoms;
m represents 6–22;
X represents an anion; and
y and z represent 1 or 2 with the proviso that yz=2.

In yet another embodiment, the invention relates to a composition for protecting human skin from harmful effects of the sun. The composition comprises a topically effective amount of a first chemical compound that absorbs ultraviolet light sufficiently to reduce significantly the damage to human skin from harmful effects of the sun and a second chemical compound having any of the structures described above, including Formula 1 or Formula 2.

In a further embodiment, the invention relates to a method for inhibiting the activity of an isoform of protein kinase C.

The method comprises contacting the protein kinase C with an effective amount of a chemical compound having any of the structures described above, including Formula 1 or Formula 2.

In yet another embodiment, the invention relates to a method for inhibiting the motility of cells. The method comprises contacting the cells with an effective amount of a chemical compound having any of the structures described above, including Formula 1 or Formula 2.

In still another embodiment, the invention relates to a method for inhibiting the metastasis of malignant cells in a mammal. The method comprises treating the mammal with an effective amount of a chemical compound having any of the structures described above, including Formula 1 or Formula 2.

In yet a further embodiment, the invention relates to a method for inhibiting the growth of pre-cancerous or malignant cells in a mammal. The method comprises treating the mammal with an effective amount of a chemical compound having any of the structures described above, including Formula 1 or Formula 2.

ABBREVIATIONS

Figure 1:
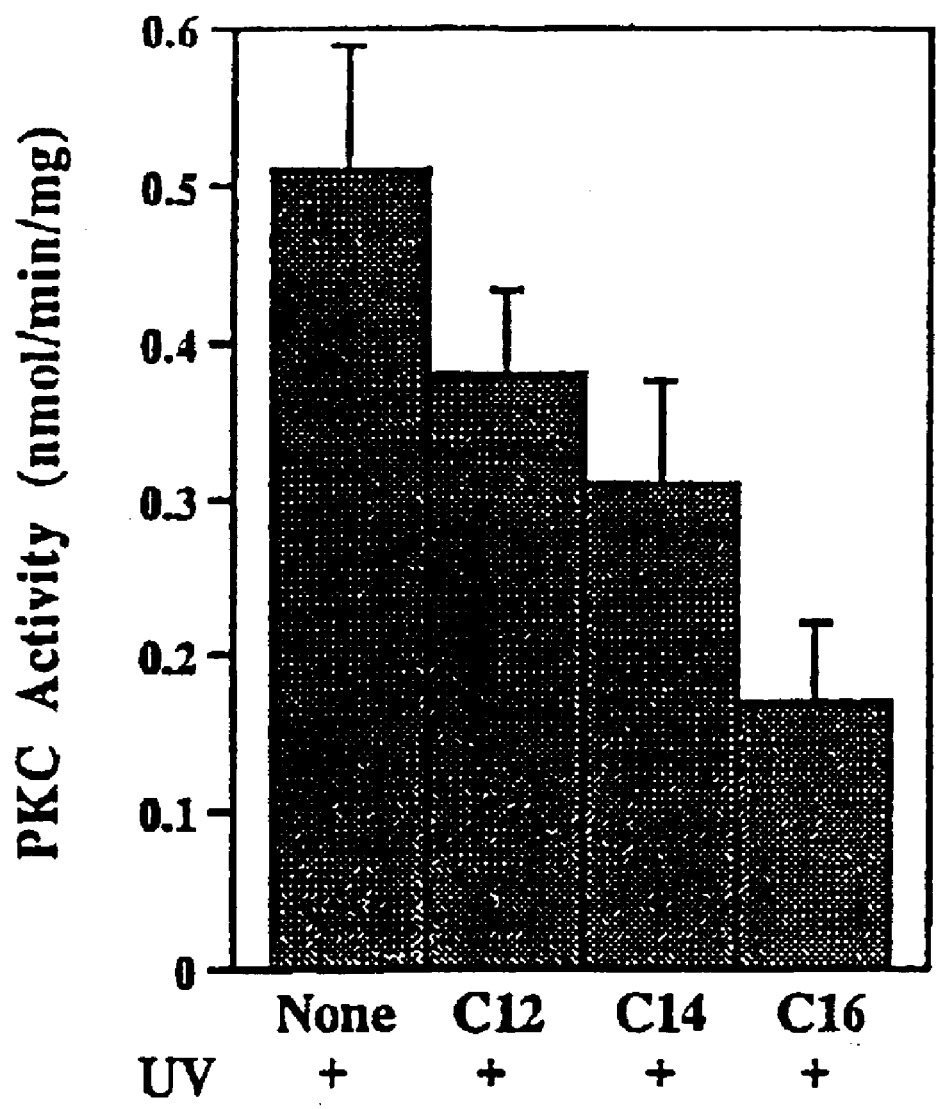
FIG. 1. Photoinduced inactivation of intracellular PKC, activity by DECA analogues. PKC activity was isolated from mouse melanoma cells that had been treated for 1 h with DMSO as a control (0.1% v/v), 250 nM C12-, C14-, or C16-DECA analogues, and irradiated for 5 min with long-wave UV light. Each value is the average of triplicate measurements.

Abbreviations used throughout the specification are defined as follows:

PKC, protein kinase C; ATP, adenosine triphosphate; PS, phosphatidylserine; TPA, 12-O-tetradecanoylphorbol-13-acetate; PMSF, phenyl methylsulfonyl fluoride; SDS-PAGE, sodium dodecyl sulfate-polyacrylamide gel electrophoresis; DMSO, dimethyl sulfoxide; UV, ultraviolet; IC50, 50% inhibitory concentration.

DECA refers to 1,1'-polymethylene-bis-4-aminoquinaldinium di-iodide. C10-DECA refers to DECA, wherein the poymethylene group is 1,10-decanediyl. C12-DECA refers to DECA, wherein the poymethylene group is 1,12-dodecanediyl, etc.

DETAILED DESCRIPTION OF THE INVENTION

In one embodiment, the invention involves novel quinoline derivatives having the formula:

(Formula 1)

or

(Formula 2)

In Formula 1 and Formula 2, Q represents a 4-E-2-$R_3$-1-quinolinium group, which has the following structure:

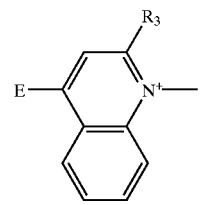

In this specification, E represents $NR_1R_2$, COO $R_1$, $OR_1$, I, Br, Cl, F, or $NO_3$; lower alkyl refers to a saturated or unsaturated alkyl group having 1–5 carbon atoms. Some examples of saturated lower alkyl groups include methyl, ethyl, n-propyl, isopropyl, n-butyl, s-butyl, t-butyl, and pentyl. Some examples of unsaturated lower alkyl groups include ethenyl, ethynyl, allyl, propenyl, propargyl, and isopropenyl. N represents a nitrogen atom. $R_1$, $R_2$, independently represent hydrogen or lower alkyl. $R_3$ represents E, hydrogen, or lower alkyl.

In a preferred embodiment, E represents $NR_1R_2$, more preferably dimethylammonium. In another preferred embodiment, $R_3$ represents lower alkyl, more preferably methyl. In an especially preferred embodiment, E represents $NR_1R_2$, more preferably dimethylammonium; and $R_3$ represents lower alkyl, more preferably methyl.

In Formula 1, L represents a chain comprising n atoms. The minimum value of n is 12, preferably approximately 14. The maximum value of n is approximately 22, preferably approximately 16. The preferred value of n is 14. In Formula 2, T represents hydrogen or a chain comprising m atoms. The minimum value of m is 6, preferably 8, more preferably 10, and most preferably 12. The maximum value of m is 22, preferably 18, more preferably 16, and most preferably 14. The preferred length of the chains is 16–17 Angstroms.

The chains contain carbon atoms and, optionally, other atoms, i.e. heteroatoms. Heteroatoms are atoms that can be bonded to two carbon atoms in a chain, and include, for example, oxygen, sulfur, and nitrogen atoms.

The number of carbon atoms in the chain is represented by t. The chain may be all carbon atoms, in which case t=n.

Alternatively, the chain may contain a mixture of carbon atoms and heteroatoms. The atoms of the chain attached to the 1 position of the quinolinium rings in Formula 1 and Formula 2 are preferably carbon atoms. Also preferably, there are at least two carbon atoms between each heteroatom.

The number of heteroatoms, if any, present in the chain, is selected on the basis of the above guidelines and parameters, in order to confer desirable properties on the compound. Desirable properties include, for example, stability, a desirable level of solubility, and improved efficacy.

The number of heteroatoms in a chain may be one or more than one. If the number of heteroatoms is more than one, the heteroatoms may all be the same, or they may be a mixture of heteroatoms.

As a general rule, the number of heteroatoms is 0 to approximately 0.5t. The words "approximately 0.5t" mean 0.5t plus or minus 0.5.

For example, the preferred maximum number of heteroatoms in a chain is four when the chain is twelve (t=8) or thirteen atoms long (t=9); five when the chain is fourteen (t=9), fifteen (t=10), or sixteen atoms long (t=11); six when the chain is seventeen (t=11), eighteen (t=12) or nineteen atoms long (t=13); and seven when the chain is twenty (t=13), twenty one (t=14), or twenty two atoms long (t=15).

The carbon atoms in the chain can be saturated or unsaturated. The unsaturated carbon atoms form at least one double bond or at least one triple bond. The double bonds are preferably trans double bonds.

The carbon atoms in the chain are, independently of each other, either unsubstituted (i.e., bonded to the requisite number of hydrogen atoms) or substituted with any one or more groups that can bind to a carbon atom. Some examples of appropriate groups include lower alkyl, phenyl, nitro, oxo, hydroxy, lower alkyloxy, lower alkylcarbonyl, lower alkylcarbonyloxy, imino, amimo, monosubstituted lower alkylamino, disubstituted lower alkylamino, lower alkylamido, thio, or lower alkylthio groups. The lower alkyl moieties in these groups are preferably methyl or ethyl.

The phenyl group may be unsubstituted. Alternatively, the phenyl group may be mono-, di-, tri, tetra, or penta-substituted with one or more groups that bind to a phenyl group. Some examples of appropriate groups include lower alkyl, nitro, nitroso, sulfate, hydroxy, lower alkyloxy, lower alkylcarbonyl, lower alkylcarbonyloxy, hydrazino, amino, monosubstituted lower alkylamino, disubstituted lower alkylamino, lower alkylamido, thio, or lower alkylthio groups.

Some examples of chains for the compounds represented by L in Formula 1 include 1,12-dodecanediyl, 1,14-tetradecanediyl, and 1,16-hexadecanediyl. Some examples of chains for the compounds represented by T in Formula 2 include 1-dodecanyl, 1-tetradecanyl, and 1-hexadecanyl. In any of these chains, any one or more of the methylene groups may be replaced by one or more heteroatom in accordance with the guidelines and parameters described above. In addition, one or both hydrogen atoms from any one or more of the methylene groups and methyl groups may be replaced by any one or more of the groups described above.

Some preferred chains containing heteroatoms comprise one or more ethylene glycol units or one or more ethylenediamine units. Some examples of chains comprising heteroatoms include those derived from polyethylene glycol (i.e. ($-CH_2CH_2O)_b CH2CH_2-$) and polyethylenediamine (i.e. ($-CH_2CH_2O)_b CH_2CH_2-$). The minimum value of b is 4. The maximum value of b is 7, preferably 6, and most preferably 5.

X in Formula 1 and 2 represents an anion. The anion can be mono, di, or trivalent. Some suitable anions include nitrate, sulfate, bisulfate, or halide (fluoride, chloride, bromide, or iodide). Other anions include phosphate, carbonate, bicarbonate, toluenesolfonate, and methanesulfonate In order to achieve overall neutrality of the compounds, w in Formula 1 represents 1 or 3, y represents 1 or 2 and z represents 1, 2 or 3, with the proviso that 2w=yz. Similarly, u and v in Formula 2 represent 1, 2, or 3 with the proviso that u=v. In other words, when z=1, y=2 and w=1; when z=2, y=1 and w=1; and when z=3, y=2 and w=3.

In a preferred embodiment, the chemical compound of the invention has the formula:

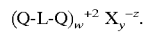

$(Q-L-Q)_w^{+2} X_y^{-z}$.

In a preferred embodiment, the chemical compound of the invention has the formula:

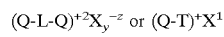

$(Q-L-Q)^{+2} X_y^{-z}$ or $(Q-T)^+ X^1$ wherein:
Q represents 4-$NR_1R_2$-2-$R_3$-1-quinolinium;
N represents a nitrogen atom;
$R_1$ and $R_2$ independently represent hydrogen or lower alkyl;
$R_3$ represents hydrogen or lower alkyl;
L represents a 1,n-aliphatic chain comprising n carbon atoms;
n represents 12–22;
T represents hydrogen or a 1,m-aliphatic chain comprising m carbon atoms;
m represents 6–22;
X represents an anion; and
y and z represent 1 or 2 with the proviso that yz=2.

In yet another embodiment of Formula 1, y and z represent 1 or 2 with the proviso that yz=2 (i.e., w=1). In yet another embodiment of Formula 2, u and v represent 1. In these embodiments, the preferred anions include nitrate, sulfate, bisulfate, or halide (fluoride, chloride, bromide, or iodide), and $R_1$, $R_2$ and $R_3$ represent hydrogen or lower alkyl.

Preferably, $(Q-L-Q)^{+2}$ represents 1,1'-(1,12-dodecanediyl)-bis(4-amino-2-methylquinolinium); 1,1'-(1,14-tetradecanediyl)-bis(4-amino-2-methylquinolinium); or 1,1'-(1,16-hexadecanediyl)-bis(4-amino-2-methylquinolinium). The preferred anion for these cations, $X_y^{-z}$, represents diiodide. The preferred compound is 1,1'-(1,14-tetradecanediyl)-bis(4-amino-2-methylquinolinium) diiodide.

In one embodiment, the invention relates to a method for inhibiting the activity of an isoform of protein kinase C. The method comprises contacting the protein kinase C with an effective amount of a chemical compound having Formula 1 or 2, as described above. The inhibition can occur in vitro (i.e., outside of a cell), ex vivo (i.e., in a cell that is not part of a living organism), or in vivo (i.e., in a cell that is part of a living organism).

The isoform can be any isoform of protein kinase C. Some isoforms include, for example, the alpha, beta 1, beta 2, gamma, delta, epsilon, eta, theta, zeta, mu, lambda/iota, etc. isoforms.

In another embodiment, the invention relates to a method for inhibiting the motility of cells. The method comprises treating the mammal with an effective amount of a chemical compound having Formula 1 or 2. The inhibition can occur ex vivo or in vivo in a mammal.

In another embodiment, the invention relates to a method for inhibiting the metastasis of malignant cells in a mammal. The method comprises treating the mammal with an effective amount of a chemical compound having Formula 1 or 2. The metastatic cells may be any of the malignant cells described above.

In still another embodiment, the invention relates to a method for inhibiting the growth of pre-cancerous cells, malignant cells, or cells that are pre-disposed to become pre-cancerous or malignant cells in a mammal. The method comprises treating the mammal with an effective amount of a chemical compound having Formula 1 or Formula 2.

Suitable mammals for any of the methods described above include farm animals, such as horses, pigs, goats, and cows; pet animals, such as dogs and cats; laboratory animals, such as mice, rats, guinea pigs, and rabbits; and primates, including humans.

The effective amount of the compound used in any of the methods described above is any amount that accomplishes the desired inhibition, i.e. inhibition of the activity of an isoform of protein kinase C in vitro, ex vivo or in vivo; inhibition of the motility of cells ex vivo and in vivo; inhibition of metastasis of malignant cells in a mammal; and/or inhibition of the growth of pre-cancerous or malignant cells in a mammal. The amount can be determined by methods known in the art. Such amounts are routinely determined by clinicians and physicians during clinical trials.

In any of the methods described above that occur in vivo, some suitable minimum amounts of the compound include, for example, approximately 0.5 mg/kg, preferably approximately 1 mg/kg, and more preferably approximately 2 mg/kg body weight of the mammal. Some suitable maximum amounts of the compound include, for example, approximately 50 mg/kg, preferably approximately 20 mg/kg, and more preferably approximately 10 mg/kg body weight of the mammal. The preferred amount is approximately 5 mg/kg body weight of the mammal.

The compound may be administered to a mammal in vivo by any known method. Some suitable methods include topically, intravenously, enterally or intraperitoneally.

The protein kinase C or the cell to be treated is exposed to a medium comprising an amount of the compound having Formula 1 or 2 that is effective to achieve the desired inhibition. In any of the methods described above that occur in vivo, the medium may be the blood of the mammal. In all cases, some suitable minimum amounts include, for example, approximately 0.05 uM and preferably approximately about 200 nM. Some suitable maximum amounts include, for example, approximately 1 uM and preferably approximately about 300 nM.

In any of the methods that treat cells ex vivo or in vivo, the cells are mammalian cells that may be pre-cancerous cells, malignant cells, or cells that are pre-disposed to become pre-cancerous or malignant cells in a mammal. Some examples of cells include melanoma cells, malignant breast, prostate, lung, uterus, kidney, and colon cells; any of the above cells in a pre-cancerous condition; and cells pre-disposed to become any of the above cells; including human cells. The method is especially effective with melanoma cells, human breast cells and pre-cancerous skin lesions.

The ex vivo or in vivo methods described above can be improved by subjecting the protein kinase C, the cells, and/or the mammal, as the case may be, as well as the chemical compound having Formula 1 or 2 to a wavelength of ultraviolet light that enhances the desired inhibition. The wavelength is any wavelength that enhances the inhibition. For example, the minimum wavelength is approximately 325 nm. The maximum wavelength is approximately 395 nm. The optimum wavelength is approximately 365 nm.

If the cells to be treated are on, in, or near the skin of a mammal, the ultraviolet light can be applied directly to the cells, such as, for example, to cutaneous lesions. Ultraviolet light may be applied to cells that are in internal organs by means known in the art, such as by optic fibers.

The amount of ultraviolet light that is applied to a surface of cells to be treated is any amount that enhances the inhibitory effect of a compound of the invention. The surface may be, for example, a layer of cells, such as a monolayer, in culture or skin.

The amount of ultraviolet radiation is any amount that enhances the inhibitory effect of a compound of the invention. For example, the minimum amount of ultraviolet radiation is approximately 1000 $\mu W/cm^2$ and preferably approximately about 1100 $\mu W/cm^2$. The maximum amount, for example, of ultraviolet radiation is approximately 2000 $\mu W/cm^2$ and preferably approximately 1700 $\mu W/cm^2$. The optimum amount of ultraviolet radiation is approximately 1200 $\mu W/cm^2$.

The time the ultraviolet light is applied to the surface of cells to be treated is any time that enhances the inhibitory effect of a compound of the invention, without causing an unacceptable level of undesirable side effects. For example, the minimum time is approximately 0.1 hours, preferably approximately 0.5 hours, and more preferably approximately 1 hour. The maximum time, for example, is approximately 5 hours, preferably approximately 3 hours, and more preferably approximately 2 hours.

In another embodiment, the invention relates to a composition for protecting human skin from harmful effects of ultraviolet light (e.g. from the sun). The composition comprises an effective amount of a first chemical compound, which absorbs ultraviolet light, in combination with an effective amount of a second chemical compound, which includes any of the compounds of the invention described above, such as Formula 1 or Formula 2. In Formula 1, n has a minimum value of 12 and a maximum value of 22. In the composition for protecting human skin from harmful effects of ultraviolet light (e.g. from the sun), n can also be from 6–11.

Preferred individual second compounds include compounds wherein $(Q-L-Q)^{+2}$ represents 1,1'-(1,10-decanediyl)-bis(4-amino-2-methylquinolinium); 1,1'-(1,12-dodecanediyl)-bis(4-amino-2-methylquinolinium); 1,1'-(1,14-tetradecanediyl)-bis(4-amino-2-methylquinolinium); or 1,1'-(1,16-hexadecanediyl)-bis(4-amino-2-methylquinolinium). Preferably, $X_y^{-z}$ represents diiodide.

The effective amount of the first chemical compound is any amount that reduces significantly the damage to human skin from harmful effects of ultraviolet light in general, and from the sun in particular. Some examples of suitable compounds that absorb ultraviolet light include p-amino benzoic acid, octyl methoxycinnamate, oxybenzone, homosalate, and octyl salicylate.

The first and second chemical compounds are formulated into compositions for topical administration to human skin, such as lotions, sprays, balms, ointments, and the like. Such formulations are described, for example, in U.S. Pat. Nos. 5,914,102 and 5,208,011, which are incorporated herein by reference.

For example, the following are listed as inactive ingredients on the label of a sunscreen lotion distributed by Schering-Plough under the trade name Coppertone: Water, PEG-8, octyl palmitate, silica, cetyl phosphate, acrylates/C10–30 alkyl acrylate crosspolymer, diazolidinyl urea, methylparaben, aloe extract, jojoba oil, tocopherol (vitamin E), propylparaben, fragrance, disodium EDTA, propylene glycol, triethanolamine, and carbomer.

The effective amount of the second chemical compound is any amount that significantly inhibits the growth of cancer cells, pre-cancer cells, or cells that are predisposed to become cancer cells or pre-cancer cells. The cells are susceptible to the ultraviolet rays of the sun when a person is exposed to the sun. Thus, the cells may exist on, in, or immediately below human skin.

Experiments described below were conducted in order to demonstrate the effect of linker length and geometry on $PKC_\alpha$ inhibition. See Example 4. The results are shown in Table 1.

In order to determine the effect of linker length, $PKC_\alpha$ inhibition was tested with DECA analogues having C6, C8, C10, C12, C14, and C16 alkyl linkers (i.e., C6-, C8-, C10-, C12-, C14-, and C16-DECA)(compounds 1a–1f, Table 1). Strict dependence between linker length and inhibitory potency was observed for analogues 1a–1f representing C6- to C14-linkers. Thus, each stepwise elongation by two carbons (2.5 Å) was accompanied by a 2-fold enhancement of potency. Maximal inhibitory potency (IC50=2.6±0.2 μM) was achieved with a linker length of C14 (1e) and C16 (1f). This value represented a 4-fold stronger inhibitory potency than 1c (IC50=11 μM), and was 20-fold stronger when compared with C6-DECA (1a) (IC50=54 μM; Table 1).

Without being bound by theory, it is believed that these findings underscore the likelihood of co-incident contact by both aromatic moieties with distinct target sites on the enzyme that are separated by a distance given by at least 14-carbons. As judged by standard bond lengths, this distance is estimated to be 16–17 Å (Table 1), which is approximately 5 Å longer than the linker present in the parent compound C10-DECA (11–12 Å).

Similarly, the spatial requirements required for potent interaction of dequalinium analogues with $PKC_\alpha$ were explored. Analogues 5 and 6 (Table 1), which bear a single site of unsaturation in the center of a C10-linker, were assayed for concentration-dependent inhibition of $PKC_\alpha$. The trans isomer (5) was the most potent (IC50=12 μM) and was indistinguishable from the saturated parent compound 1c, whereas the IC50 value for the cis (6) isomer was 52 μM.

It was noted that the trans geometry of the linker probably does not itself contribute to potency, since the trans-5-decene C10-monomer (4) was no more potent than the saturated C10-monomer (2) (Table 1).

The disparate inhibitory potencies observed for the trans and cis unsaturated dimers (5 and 6) suggest that the geometry of the linker may affect correct positioning of the aromatic rings with the enzyme. Comparison of energy minimized structures of the saturated C10-DECA with the cis and trans isomers indicate that the cis conformation is significantly different from the similar conformations obtained for the saturated and trans compounds. Moreover, the conformation for the cis isomer exhibits a pyridinium-pyridinium distance (12.7 Å) that is approximately 1 Å shorter than the analogous distance in the trans isomer (13.7 Å) and saturated C10-DECA (14 Å). The lower inhibitory potency observed for the cis isomer therefore correlates with a decreased pyridinium-pyridinium distance and an altered spatial relationship of the aromatic ring moieties.

In order to determine the effect of linker length ex vivo, UV irradiation was successfully employed to inactivate intracellular PKC with DECA in metastatic B16 F10 melanoma cells. The procedure is described in Example 5. PKC is the only $Ca^{2+}$— and phospholipid-dependent isoform expressed by these cells, and it is present in high abundance. B16 F10 cells were treated with 250 nM of C12-, C14- or C16-DECA, and followed by treatment with longwave light to photolyze the analogue in situ. Cell lysates were prepared that were partially purified by DEAE-Sephacel chromatography and then assayed for $Ca^{2+}$/phospholipid-dependent PKC activity. The results (FIG. 1) demonstrated that linker-length dependent inhibition of PKC activity was evident with 250 nM of each analogue, where the highest extent of PKC inhibition was typically 40–60% of the total PKC activity. The pattern of inactivation of intracellular PKC activity reflected the same rank order of inhibitory potencies observed in vitro for these analogues (Table 1).

TABLE 1

Linker Distance and Geometry of Dequalinium Analogues Determine Inhibitory Potency with Protein Kinase Cα[a]

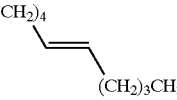

| Compound | | IC50 (μM)[b] | Spacer (Å)[c] | |
|---|---|---|---|---|
| 1a | Q(CH$_2$)$_6$Q | 54 ± 8 | 6.4 | |
| 1b | Q(CH$_2$)$_8$Q | 25 ± 9 | 8.8 | |
| 1c | Q(CH$_2$)$_{10}$Q | 11 ± 5 | 11.5 | parent compound |
| 1d | Q(CH$_2$)$_{12}$Q | 5 ± 2 | 14.0 | |
| 1e | Q(CH$_2$)$_{14}$Q | 2.6 ± 0.2 | 16.6 | |
| 1f | Q(CH$_2$)$_{16}$Q | 2.8 ± 0.2 | 19.1 | |
| 2 | Q(CH$_2$)$_9$CH$_3$ | 117 ± 8 | — | monomer |
| 3 | QCH$_3$ | 3590 ± 510 | — | monomer |
| 4 | Q(CH$_2$)$_4$\\(CH$_2$)$_3$CH$_3$ | 137 ± 6 | — | monomer |

TABLE 1-continued

Linker Distance and Geometry of Dequalinium Analogues Determine
Inhibitory Potency with Protein Kinase Cα[a]

Q = (4-amino-2-methylquinolinium iodide structure, H$_2$N— at 4-position, CH$_3$ at 2-position, N$^+$ with I$^-$)

| Compound | | IC50 ($\mu$M)[b] | Spacer (Å)[c] |
|---|---|---|---|
| 5 | Q(CH$_2$)$_4$ / (CH$_2$)$_4$Q (trans) | 12 ± 3 | 11.1 |
| 6 | Q(H$_2$C)$_4$ / (CH$_2$)$_4$Q (cis) | 52 ± 12 | 10.5 |

[a]Assays were performed under conditions of reversible binding as described in the 'Methods.'
[b]IC50 represents the analogue concentration producing 50% inhibition. Each IC50 value is the average of two or more independent experiments (±s.d.), where each experiment consisted of triplicate measurements of PKC$_\alpha$ activity.
[c]For each alkyl linker consisting of n carbons, the distance (d) between the terminal alkane carbons was measured from energy minimized structures with PCModel v6.0 and using standard bond length values where d = (n-1)1.25 Å.

As with the in vitro experiments described above, the linker distance between the two aromatic moieties proved to be an important variable ex vivo. The potency of inhibition of PKC$_\alpha$ with analogues containing C6–C16 linkers revealed a length-dependency that reached a plateau at IC50=2.5 $\mu$M with C14-DECA, representing a linker distance of 16 Å. This finding suggests that the additional linker distance between the aromatic moieties in C14-DECA facilitates binding to their tandem sites in PKC with greater efficiency than the parent compound C10-DECA, which has a linker distance of 11–12 Å. The notion of a two-point contact by DECA compounds may explain the weak or absent inhibition by DECA with other protein kinases, such as PKA, that have closely related catalytic domains but apparently lack one or both binding sites.

The divergent inhibitory potencies observed for the cis and trans C10-linker analogues were not simply the outcome of slight differences in linker distance. Based on a series of DECA analogues for which the relationship of saturated alkyl linker length (from standard bond lengths) and potency had been established (Table 1), the distance for each unsaturated linker was used to predict the potency of the resulting DECA analogue. If linker distance were the sole determinant of inhibitory potency, then the cis compound (6), whose linker length (10.5 Å) is close to that of a saturated C9-analogue (10.2 Å), should have exhibited a potency of approximately 25 $\mu$M rather than the observed 52 $\mu$M. The substantial departure between the predicted and observed potencies for the cis analogue (6) suggests that the geometry of the linker itself may in part determine the productive binding of each analogue, and consequently the extent of enzyme inhibition. By contrast, the trans isomer (5) exhibited both a linker distance (11.1 Å) and an inhibitory potency (IC50=12 $\mu$M) that closely mimicked those of the saturated parent compound 1c (11.5 Å and IC50=11–12 $\mu$M, respectively). This concordance implies that a trans-oid geometry of the linker disposes the aromatic groups to bind productively. Energy-minimized structures of the saturated, cis and trans analogues are consistent with the experimental findings and support a model in which the most effective binding of the aromatic moieties to the enzyme occurs in a trans-oid manner.

Thus, the efficacy of DECA analogues with PKC, in vitro was reproduced in metastatic murine B16 melanoma cells with UV light to render the drug photoreactive. See above. Photoreactivity of the drug, in turn, causes irreversible inhibition of PKC$_\alpha$, as was previously described for C10-DECA[1]. Photoactivation of the drug potentiated the action of DECA in melanoma cells such that intracellular PKC inhibition could be detected with nanomolar concentrations of the drug. As judged by assay of PKC activity partially purified from cell lysates, irreversible inhibition of intracellular PKC$_\alpha$ provided the means by which to compare the effects of 250 nM C12-, C14- and C16-DECA analogues. The improved response to analogues as a result of a longer linker is consistent with the improved sensitivity of PKC, observed in vitro (Table 1). The observed patterned response produced by 250 nM DECA analogues with intracellular PKC is similarly reflected in the inhibition of motility of melanoma cells in vitro. Therefore, UV-assisted treatment offers a therapeutic approach to inhibit metastatic behavior of melanoma cells.

The role of intracellular PKC activity in the motility of metastatic murine melanoma B16 F10 cells, and as a target for DECA analogues with increasing PKC inhibitory potencies was demonstrated using the procedure of Example 6. Pre-treatment of a monolayer of B16 F10 cells with 250 nM DECA analogues in the presence of UV irradiation for 5 min, resulted in: 1) complete inhibition of cell motility for up to 4 h in a time-lapse motility assay, and 40–60% inhibition of cell migration in a Boyden chamber; and 2) inhibition by 40–60% of intracellular PS/Ca$^{2+}$-dependent PKC catalytic activity, signifying inactivation of a conventional PKC isoform. Because $PKC_\alpha$ is the only conventional PKC isoform detected in B16 F10 cells, a stably transfected clone expressing a kinase-defective mutant of PKC, was developed that exhibited a substantial loss of adhesion and motility, and was refractory to further inhibition by DECA. These findings identify $PKC_\alpha$ catalytic activity both as a mechanistic component of cell motility and adhesion, and as a critical intracellular target of DECA analogues. These studies demonstrate that the combined use of UV with nanomolar concentrations of DECA offers an effective chemotherapeutic approach to inhibit metastatic behavior of melanoma cells.

Photo-induced inactivation is demonstrated with intracellular PKC in cells that have been treated with a compound according to the invention, and irradiated directly with longwave UV light. A novel aspect is that UV-induced inhibition of both PKC activity and cell motility can be observed with nanomolar concentrations. These studies implicate $PKC_\alpha$ as a critical component in the motility of metastatic melanoma cells, and establish it as an important target for anti-metastatic agents.

Figure 2A:
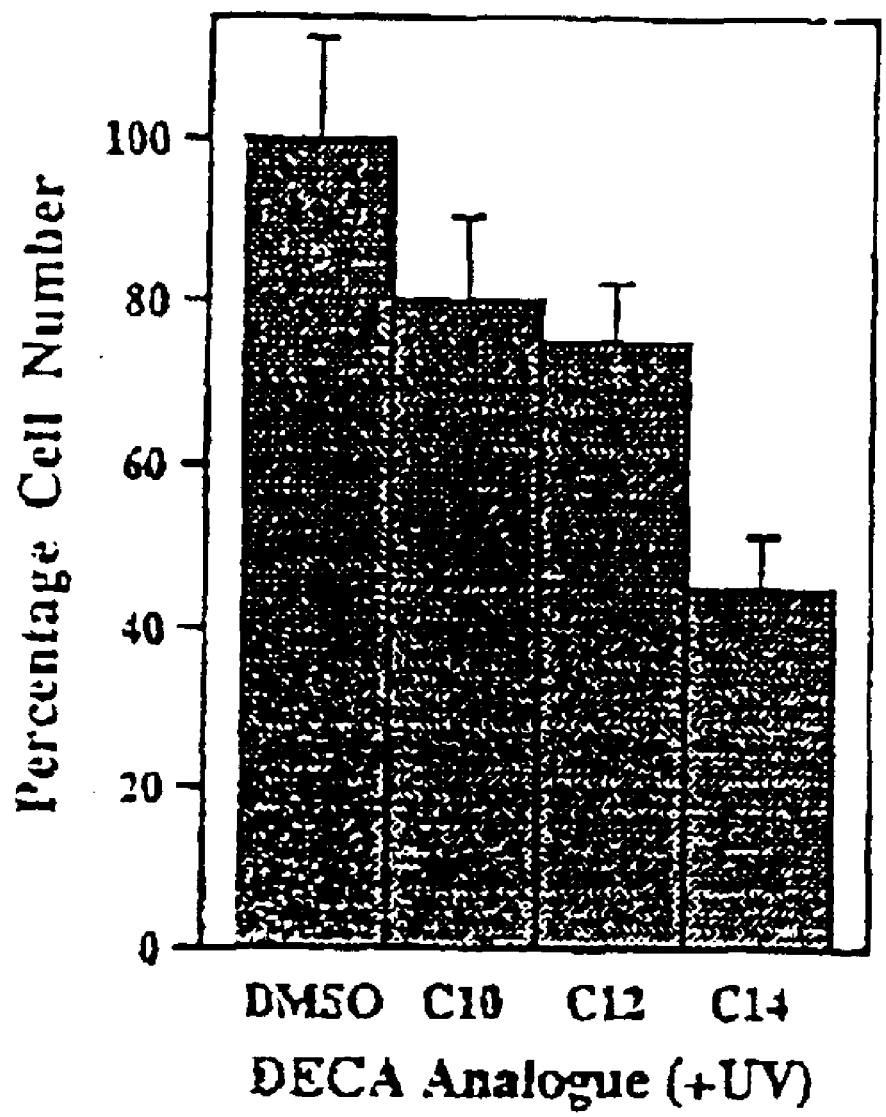
FIG. 2. Inhibition of cell migration by DECA analogues. (A) Cells were treated with C10-(control), C12-, or C14-DECA analogues at 250 nM for 1 h, followed by UV irradiation for 5 min. Cells were assayed for migration in transwells. Each value is the average of triplicate measurements where the standard deviation was within 15%. (B) Concentration-dependent inhibition of cell migration by C14-DECA. Cells were treated with the indicated concentrations of C14-DECA. The results are representative of three independent experiments. For both (A) and (B), analysis of variance showed the P<0.001.
Figure 3A:
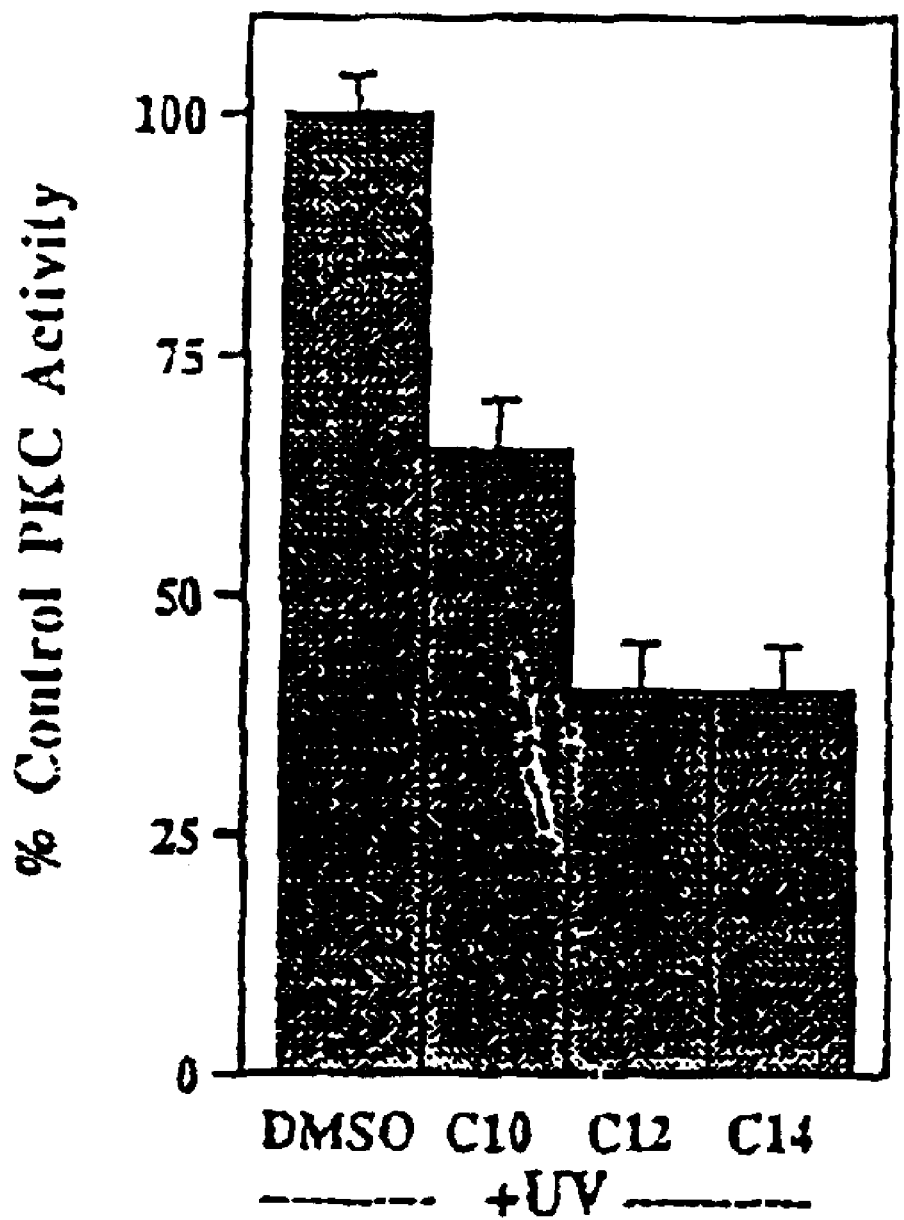
FIG. 3. Inactivation of intracellular PKC activity by DECA analogues. PKC activity was partially purified from cells that had been treated with a DECA analogue and UV irradiation, and then assayed for catalytic activity. The average of triplicate activity measurements was typically within 10–15% error. Each experiment is representative of two or more independent experiments. (A) Inhibition of intracellular PKC activity was analyzed following treatment of cells with UV plus 250 nM C10-(control), C12-, C14-DECA, or DMSO (0.05% v/v). (B) Inhibition of PKC activity by C14-DECA is potentiated with UV light. The control TPA/PS/$Ca^{2+}$-dependent kinase activity (165 pmol/min/mg) isolated from vehicle-treated cells (0.05% DMSO), was compared with 5 min UV irradiation only, 250 nM C14-DECA only, or the combination of these treatments. The percentage control PKC activity remaining after each treatment is shown.
Figure 3B:
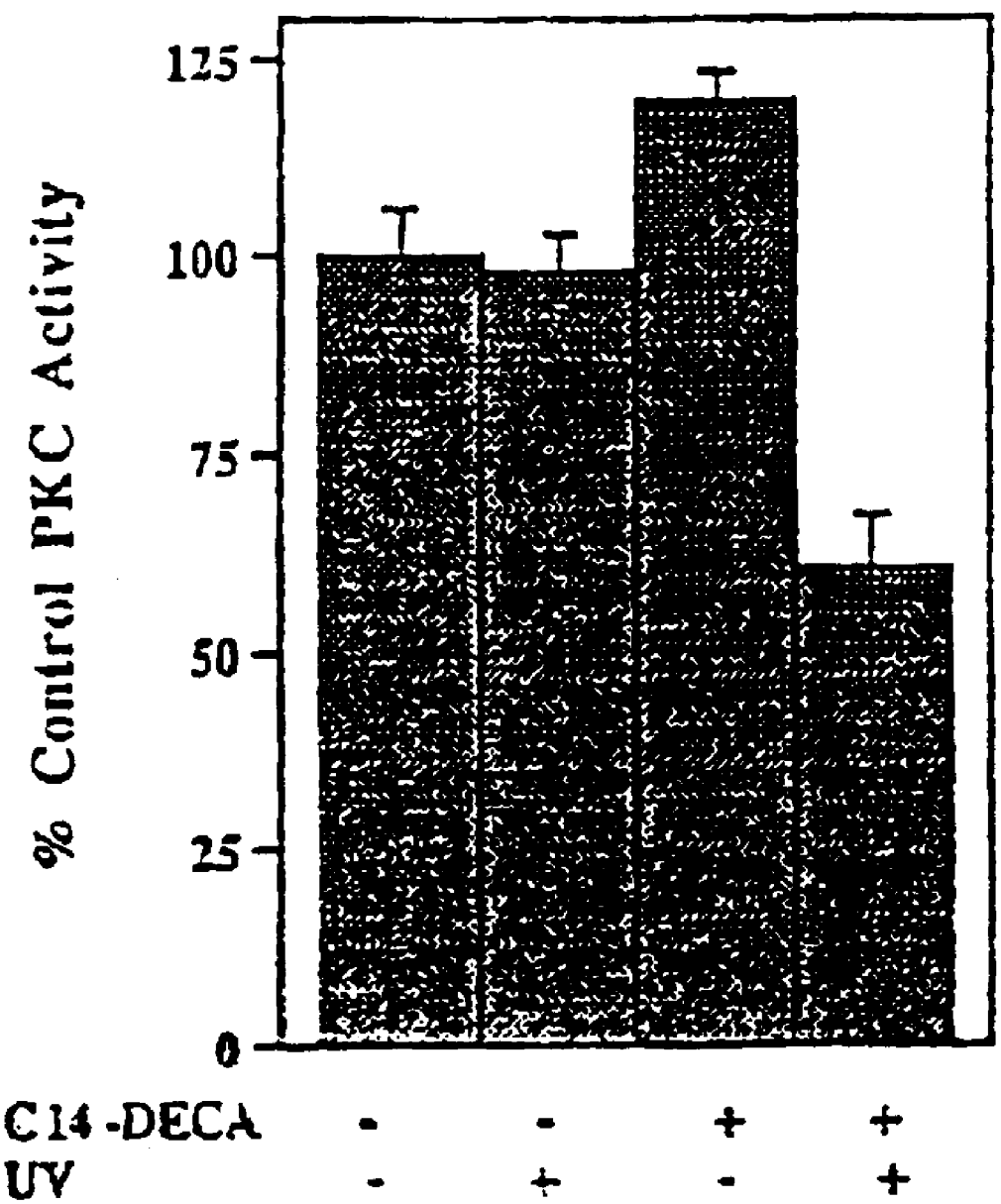

Inactivation of intracellular PKC by nanomolar concentrations of DECA analogues under the same conditions that produce inhibition of cell motility was demonstrated in accordance with the procedure of Example 8. B16 F10 cells were treated with 250 nM of either C10-(control), C12-, or C14-DECA, and irradiated with UV for 5 min. The results (FIG. 3A) demonstrated that 250 nM C10-DECA produced 35% inhibition of $TPA/PS/Ca^{2+}$-dependent PKC activity. This finding is consistent with a 33% loss of cell motility and 20–30% inhibition of cell migration (FIG. 2A) produced by C10-DECA under identical conditions. In comparing FIGS. 2A and 3A, it can be seen that the C14-DECA analogue showed greater potency than C10-DECA in inhibition of both motility and PKC activity. However, the C12-DECA analogue, which occasionally produced an intermediate effect in inhibiting these activities, exhibited less predictable activity. Nonetheless, inactivation of PKC activity by 250 nM C14-DECA plus Uv typically produced 40–60% inhibition, whereas UV light alone or 250 nM C14-DECA alone had no inhibitory effect (FIG. 3B). Thus, an improvement in inhibitory potency was consistently observed when comparing C14-DECA and C10-DECA for inhibition of both PKC activity and migration.

Inactivation of PKC activity was maximal with 5-min irradiation. Longer periods of irradiation (up to 30 min) neither improved nor diminished the extent of PKC inhibition.

EXAMPLES

Example 1

Materials

All solvents were distilled before use and dried over sodium benzophenone ketal. Hexamethylphosphoramide (HMPA) was distilled from $CaH_2$ prior to use. With the exception of 5-Hexyn-1-ol (Farchan Laboratories), all reagents were purchased from Aldrich. Silica gel 60 (230–400 ASTM) was used for flash chromatography. TLC was carried out using Merck silica gel 60 aluminum-backed plates. $^1H$ and $^{13}C$ NMR were recorded on a Bruker NMR spectrometer at 400 and 100 MHz, respectively.

Example 2

Synthesis of DECA Analogues

Synthesis of DECA analogues was carried out by established methods[2,13,14]. Synthesis of unsaturated linkers for the compounds was carried out by reduction (Lindlar catalyst and Birch reaction, respectively) of the 1,10-alkyne diol, which had been prepared by a previously described method[11]. Saturated linkers were commercially available as diols and were converted to di-iodides[12]. Alkylation of each alkyl linker by 4-amino-2-methylquinoline (present in 3-fold stoichiometric excess) was carried out in 2–10 ml 2-butanone at 95° C. for 48 h. The product, which precipitates out of solution as a di-iodide salt, was filtered and washed three times with 5–10 mL 2-butanone. Synthesis of DECA analogues wherein one or more heteroatom (N, O, S) replace an equivalent number of methylene groups are prepared by the same methods described above.

Example 3

Characterization of DECA Analogues

Product compounds were analyzed for purity by HPLC on a Waters Delta-Pak C18 reverse-phase column (2×150 mm; 300 Å), using an acetonitrile gradient (0–60% acetonitrile) in water for 1 h. By this analysis, each product was judged to be >90% pure. As demonstrated by HPLC, the isomeric purity of the trans compound 6 was nearly 100%. The cis isomer 5 however, contained 17% of 6, and was therefore composed of a 5:1 cis:trans ratio. Compounds were analyzed by $^1H$ using a Bruker NMR spectrometer at 400 MHz, and by low resolution electrospray ionization-mass spectrometry.

1,1'-[(E)-5-Decene-1,10-diyl]bis[4-amino-2-methyl]quinolinium, diiodide (5). $^1H$ NMR (DMSO-$d_6$) δ 1.52 (m, 4H), 1.74 (m, 4H), 2.10 (m, 4H), 2.72 (br s, 6H), 4.46 (m, 4H), 5.45 (m, 2H), 6.72 (br s, 2H), 7.72 (m, 2H), 8.00 (m, 2H), 8.14 (m, 2H), 8.45 (m, 2H), 8.84 (br s, 4H). Elemental analysis Calcd for $C_{30}H_{38}N_4I_2$: C, 50.86%; H, 5.41%; N, 7.91%. Found: C, 50.82%; H, 5.30%; N, 6.97%. MS, $[M-2I^-]=227.1$ (m/z) (calcd 227.32 for $C_{30}H_{38}N_4$).

1,1'-[(Z)-5-Decene-1,10-diyl]bis[4-amino-2-methyl]quinolinium, diiodide (6). $^1H$ NMR (DMSO-$d_6$) δ 1.52 (m, 4H), 1.74 (m, 4H), 2.10 (m, 4H), 2.72 (br s, 6H), 4.46 (m, 4H), 5.40 (m, 2H), 6.72 (br s, 2H), 7.72 (m, 2H), 8.00 (m, 2H), 8.14 (m, 2H), 8.45 (m, 2H), 8.84 (br s, 4H). Elemental analysis Calcd for $C_{30}H_{38}N_4I_2$: C, 50.86%; H, 5.41%; N, 7.91%. Found: C, 50.88%; H, 5.28%; N, 7.76%. MS, $[M-2I^-]=227.1$ (m/z) (calcd 227.32 for $C_{30}H_{38}N_4$).

1,1'-(1,12-Dodecanediyl)bis[4-amino-2-methyl]quinolinium, diiodide (1d). $^1H$ NMR (DMSO-$d_6$) δ 1.35(br s, 8H), 1.40 (m, 4H), 1.48 (m, 4H), 1.73 (m, 4H), 2.75 (s, 6H), 3.35 (br s, 4H), 4.45 (t, J=7.7 Hz, 4H), 6.75 (s, 2H), 7.72 (t, J=7.7 Hz, 2H), 8.05 (t, J=7.7 Hz, 2H), 8.15 (d, J=8.0 Hz, 2H), 8.45 (d, J=8.0 Hz, 2H), 8.85 (br s, 4H). Elemental analysis Calcd for $C_{32}H_{44}N_4I_2$: C, 52.09%; H, 6.01%; N, 7.59%. Found: C, 51.52%; H, 6.08%; N, 7.13%. MS, $[M-2I^-]=242.1$ (m/z) (calcd 242.35 for $C_{32}H_{44}N_4$).

1,1'-(1,14-Tetradecanediyl)bis[4-amino-2-methyl]quinolinium, diiodide (1 e). $^1H$ NMR (DMSO-$d_6$) d 1.30 (br s, 8H), 1.35 (m, 4H), 1.45 (m, 4H), 1.75 (m, 4H), 2.75 (s, 6H), 3.35 (m, 4H), 4.47 (m, 4H), 6.75 (s, 2H), 7.72 (t, J=7.7 Hz, 2H), 8.05 (t, J=7.7 Hz, 2H), 8.15 (d, J=8.0 Hz, 2H), 8.45 (d, J=8.0 Hz, 2H), 8.85 (br s, 4H). $^{13}C$ NMR (DMSO-$d_6$) d 24.31, 28.57, 30.75, 31.53, 31.71, 31.75, 50.65, 106.61, 106.68, 119.25, 119.31, 121.14, 127.01, 128.61, 136.56, 141.72, 157.72, 159.37, 159.43. Elemental analysis Calcd for $C_{34}H_{48}N_4I_2$: C, 53.27%; H, 6.31%; N, 7.31%. Found: C, 52.93%; H, 6.30%; N, 6.93%. MS, $[M-2I^-]=256.2$ (m/z) (calcd 256.38 for $C_{34}H_{48}N_4$)

1,1'-(1,16-Hexadecanediyl)bis[4-amino-2-methyl]quinolinium, diiodide (1f). $^1H$ NMR (DMSO-$d_6$) δ 1.30 (m, 16H), 1.45 (br s, 4H), 1.73 (br s, 4H), 2.74 (s, 6H), 3.34 (br s, 4H), 4.46 (m, 4H), 6.74 (s, 2H), 7.73 (t, J=7.5 Hz, 2H), 8.02 (t, J=8.2 Hz, 2H), 8.16 (d, J=8.9 Hz, 2H), 8.44 (d, J=8.2 Hz, 2H), 8.83 (br s, 4H). $^{13}$C NMR (DMSO-$d_6$) □ 26.53, 30.80, 32.98, 33.57, 33.93, 34.00, 52.88, 108.85, 108.91, 121.49, 121.55, 123.37, 129.25, 130.84, 139.36, 143.96, 159.96, 161.68. Elemental analysis Calcd for $C_{36}H_{52}N_4I_2$: C, 54.41%; H, 6.59%; N, 7.05%. Found: C, 53.94%; H, 6.68%; N, 6.65%. MS, [M-2I$^-$]=270.2 (m/z) (calcd 270.41 for $C_{36}H_{52}N_4$).

N-Decyl-4-aminoquinaldinium iodide (2). This compound was prepared by mixing commercially available iododecane and 4-aminoquinaldine in methyl ethyl ketone, and refluxing for 72 h. The solid product was collected by filtration and recrystallized twice in absolute ethanol. $^1$H NMR (in DMSO-$d_6$): δ 0.85 (t, J=5.1 Hz, 3H), 1.24 (br, 12H), 1.43 (m, 2H), 1.70 (m, 2H), 2.73 (s, 3H), 4.45 (t, J=8.09 Hz, 2H), 6.73 (s, 1H), 7.72 (dd, 1H), 8.02 (dd, 1H), 8.15 (d, J=8.94 Hz, 1H), 8.43 (d, J=8.37 Hz), 8.81 (br, 2H). Elemental analysis Calcd for $C_{20}H_{31}N_2I$: C, 56.33%; H, 7.33%; N, 6.57%. Found: C, 56.23%; H, 7.41%; N, 6.42%. MS, [M-I$^-$]=299 (m/z) (calcd 299.47 for $C_{20}H_{31}N_2$).

Stock solutions for DECA analogues were prepared in DMSO and standardized spectrophotometrically (333 nm) on a Perkin-Elmer Lambda II spectrophotometer using a molar extinction coefficient of 13,500 for monomeric analogues, and 27,000 for dimeric analogues.

Example 4

Assay of PKC$_\alpha$ Catalytic Activity in Vitro

Recombinant human PKC$_\alpha$ (>95% pure) (PanVera Corp., Madison, Wis.) was used for testing DECA analogues in vitro. Total PKC, catalytic activity (36 ng protein) and the indicated concentration of DECA analogue was measured in triplicate in the presence of activating cofactors (10 μg phosphatidylserine, 0.5 mM Ca$^{2+}$) by the transfer of $^{32}$P from [γ-$^{32}$P]-ATP to the modified pseudosubstrate peptide (RFARKGSLRQKNV), as described elsewhere[1]. For assay of partially purified B16 F10 cell lysates (25 μg/assay), PKC activity was taken as the difference in phosphotransferase activity measured in triplicate in the presence and absence of activating cofactors (10 μg phosphatidylserine, 0.5 mM Ca$^{2+}$) as previously described[2].

Example 5

Inactivation of PKC$_\alpha$ in Murine Melanoma Cells with Ultraviolet Radiation and DECA Analogues Murine melanoma B16 F10 cells were cultured in 15 cm$^2$ dishes to 75–80% confluence in RPMI medium containing 10% fetal bovine serum, 1% penicillin/streptomycin, and 0.125 μg/ml fungizone. Prior to drug application, cells were washed twice with phosphate buffered saline (PBS) and were restored in serum-free medium containing either DMSO (0.1% v/v) or 250 nM C12-, C14-, or C16-DECA analogue. Monolayers of cells were treated with or without the indicated DECA analogue for 1 h and irradiated for 5-min (1200 UV/cm$^2$) with a UV lamp (American Ultraviolet Co., Murray Hill, N.J.). Following this treatment, the medium was removed and the cells were washed twice with PBS. Preparation of cell lysates was followed by partial purification by DEAE-Sephacel chromatography, as previously described[2].

Example 6

Cell Motility Assay

To measure cell motility by digital image capture, an Olympus IMT-2 inverted phase contrast microscope (Olympus Microscopes, UK), fitted with a Fujitsu TC2-336P CCD camera (EOS Electronics AV Ltd, Barry, Wales) and surrounded by a perspex temperature-regulated jacket that was adjusted to 37° C. Cells were plated onto 3-cm$^2$ petri dishes such that a densely confluent monolayer was achieved within 24 or 48 h. Following treatment of cells with C10-DECA and UV, a 'scratch wound' was created by drawing a sterile micro-pipette tip along the monolayer using a ruler as a guide. Detached cells were removed by washing twice in growth medium before adding 2 ml fresh medium. The dish was placed in a specially constructed 2-piece circular aluminum housing which had a glass lid and an epicentric hole in the base through which the cells were observed using the 10×objective. The chamber was gassed with 10% CO$_2$ in humidified air and was placed onto the stage of the microscope. A regular wound edge was chosen and digital images were collected every 30 min for 8 h onto a Power Mac 7100 using Adobe Premier software. The percentage of the capture window (determined as 726 μm×544 μm) that had been filled in by the movement of cells (normalized to the original wound edge) was determined with Optilab software and plotted against time.

Example 7

Inhibition of Migration of Murine Melanoma by DECA Analogues

A 12-mm Costar transwell (Boyden chamber) having a 12-μm pore size was used to measure cell movement across a porous polycarbonate membrane. The bottom surface was coated with 35 μg Matrigel for 1 h at 37° C., 5% CO$_2$. Cells were seeded into the upper chamber of the transwell at 10$^5$ cells/well and incubated at 37° C., 5% CO$_2$. Following incubation for 3 h, the upper chamber was carefully wiped with a cotton swab in order to remove cells that remained on the upper membrane surface. Those cells that had migrated to the lower membrane surface were fixed and stained by the H+E Method (Fisher Diagnostics Leukostat). By use of a Nikon Diaphot-TMD inverted microscope at 400× magnification, eight fields of adherent cells were randomly counted in each well and numerically averaged. Each condition was conducted in triplicate and statistical significance was determined by ANOVA using SigmaStat software.

Figure 2B:
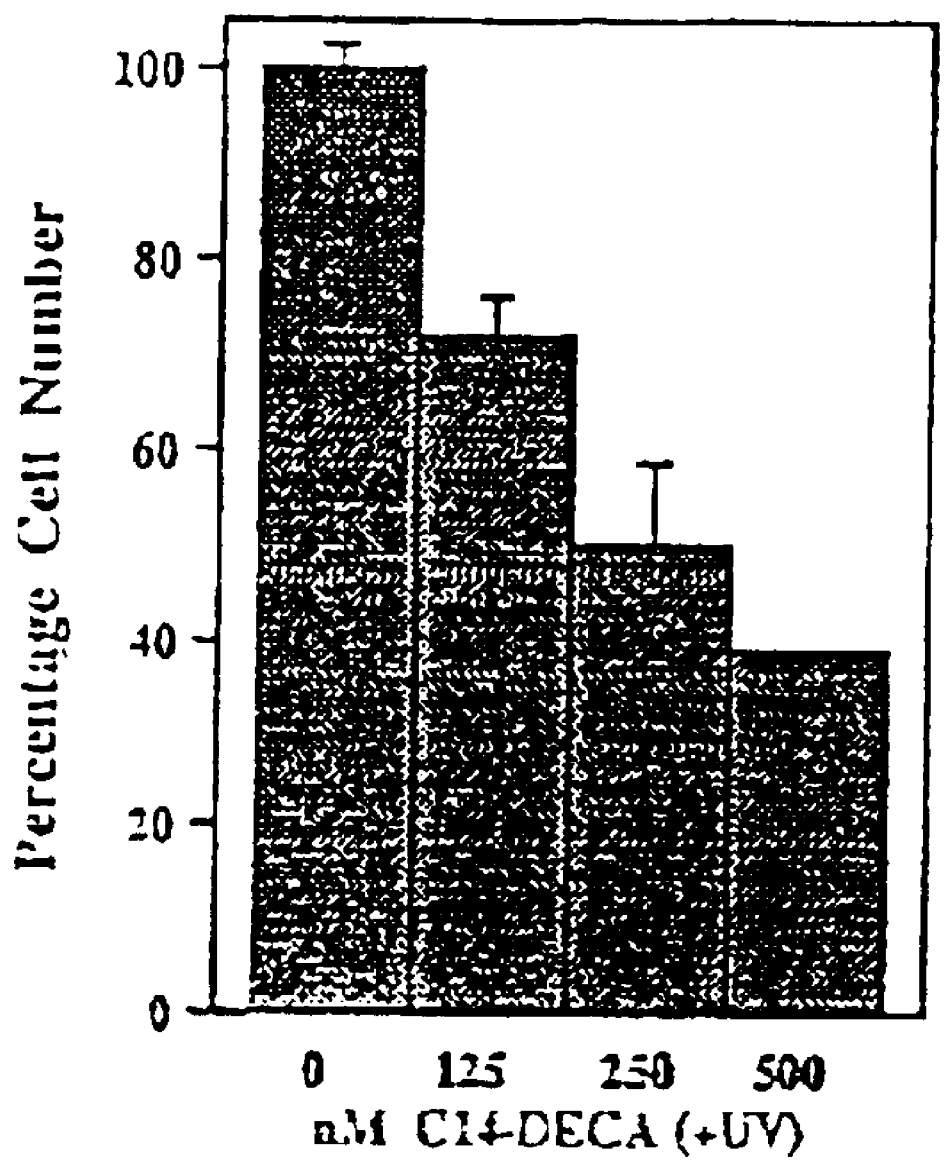

Inhibition of cell migration by 250 nM DECA analogues (C10-(control), C12-, and C14-DECA) was analyzed during the initial 3 h post-treatment by the use of Boyden chambers. Cells that had been treated with a DECA analogue plus UV were applied to the upper surface of the membrane whereupon they moved chemotactically through the membrane, and adhered to Matrigel, which had been coated onto the under surface of the membrane. Following the initial 3 h, the number of cells migrating to this lower surface was measured. As can be seen in FIG. 2A, DECA analogues produced inhibition of cell migration and exhibited a patterned response with analogues having longer linkers. Although 250 nM C10-DECA inhibited migration by 20–30% of controls, inhibition by 250 nM C14-DECA was more potent, producing 40–60% of the control. Additional experiments indicated that inhibition by C14-DECA was dose-dependent in the range of 0–500 nM, as shown in FIG. 2B.

Example 8

Inactivation of Murine Melanoma Motility and PKC Activity with Ultraviolet Irradiation and DECA Analogues A confluent monolayer of cells was washed twice with PBS and the indicated concentration of DECA analogue was added to the cells in serum-free medium. Cells were treated with or without the drug for 1 h at 37° C., 5% $CO_2$, followed by washing with PBS. In PBS and with the lids off, cells were irradiated with longwave UV light for 5-min (1200 $\mu W/cm^2$). Irradiation was carried out with a longwave UV lamp (American Ultraviolet Co., Murray Hill, N.J.) while the plate of cells were subjected to gentle shaking at room temperature. Following this treatment, the medium was removed and the cells were washed twice with PBS. At this point, cells were collected for subsequent assay of adhesion or migration (see below), or lysed for PKC isolation.

To isolate PKC, cells were harvested by scraping, pelleted, and lysed in homogenization buffer containing 0.1% Triton X-100. The sample was applied to a 0.5-ml column of DEAE-Sephacel, the column was washed with Buffer A (20 mM Tris, pH 7.5, 2 mM EGTA, 2 mM EDTA, 1 mM 2-mercaptoethanol, 0.25 mM PMSF, 10 $\mu g/ml$ leupeptin, and 10 $\mu g/ml$ soybean trypsin inhibitor), and PKC activity was recovered by elution with 150 mM NaCl in Buffer A, as previously described PKC catalytic activity was judged by a standard assay in which $^{32}P$ was transferred from $[\gamma\text{-}^{32}P]$-ATP to a peptide substrate, as described elsewhere[2]. Triplicate measurements of substrate phosphorylation were conducted in the absence and presence of 1 $\mu M$ TPA, 83 $\mu g/ml$ PS, and 0.5 mM $Ca^{2+}$. The difference in substrate phosphorylation in the two conditions was taken as PKC activity. The peptide substrate used in these studies was the synthetic modified pseudosubstrate peptide ($^{25}Ser$ peptide)[15].

Example 9

Experimental Metastasis in Mice

C57BL/6 mice of comparable age and weight were used in each of two experimental groups consisting of 8 animals per group. In preparation for tail vein injections, mice were tranquilized with 0.2 mg of acepromazine via i.p. injections. B16F10 cells obtained from ex-vivo culture were injected into the tail vein ($10^5$ cells/0.2 ml). Animals were treated IP with vehicle (0.36% sodium citrate) or 5 mg/kg of C14-DECA on the day of the tail vein injection and every other day thereafter for a 2–3 week experiment. At the end of the experimental period, the mice were sacrificed by $CO_2$ asphyxiation. The lungs were removed and placed in 10% formalin until the metastatic nodules were counted using a dissecting microscope.

The results showed that animals that were treated with dequalinium-14 every other day for a period of 2 weeks, displayed 40% fewer pulmonary nodules.

REFERENCES

[1] Rotenberg, S. A.; Sun, X.-g. Photo-induced inactivation of protein kinase C by dequalinium identifies the RACK-I binding domain as a recognition site. *J. Biol. Chem.* 1998, 273, 2390–2395.
[2] Rotenberg, S. A.; Smiley, S.; Ueffing, M.; Krauss, R. S.; Chen, L. B.; Weinstein, I. B. Inhibition of rodent protein kinase C by the anticarcinoma agent dequalinium. *Cancer Res.* 1990, 50, 677–685.
[3] Rotenberg, S. A., and Weinstein, I. B. (review article). Protein kinase C in neoplastic cells. In: *Biochemical and Molecular Aspects of Selected Cancers*, 1991, 25–73, Academic Press, Orlando.
[4] Weiss, M. J.; Wong, J. R.; Ha, C. S.; Bleday, R.; Salem, R. R.; Steele, G. D.; Chen, L. B. Dequalinium, a topical antimicrobial agent, displays anticarcinoma activity based on selective mitochondrial accumulation. *Proc. Natl. Acad. Sci.* 1987, 84, 5444–5448.
[5] Chen, L. B.; Mitochondrial membrane potential in living cells. *Ann. Rev. Cell Biol.* 1989, 4, 155–181.
[6] Bernal, S. D.; Lampidis, T. J.; McIsaac, R. M.; Chen, L. B. Anticarcinoma activity in vivo of rhodamine 123, a mitochondrial-specific dye. *Science* 1983, 222, 169–172.
[7] Rotenberg, S. A.; Zhu, J.; Hansen, H.; Li, X.-d.; Sun, X.-g.; Michels, C. A.; Riedel, H. Deletion analysis of protein kinase C, reveals a novel regulatory segment. *J. Biochem.* 1998, 124, 756–763.
[8] Zhuo, S.; Allison, W. S. Inhibition and photoinactivation of the bovine heart mitochondrial F1-ATPase by the cytotoxic agent, dequalinium. *Biochem. Biophys. Res. Comm.* 1988, 152, 968–972.
[9] Bodden, W. L.; Palayoor, S. T.; Hait, W. N. Selective antimitochondrial agents inhibit calmodulin. *Biochem. Biophys. Res. Commun.* 1986, 135, 574–582.
[10] Galanakis, D.; Ganellin, C. R.; Malik, S.; Dunn, P. M. Synthesis and pharmacological testing of dequalinium analogues as blockers of the apamin-sensitive $Ca^{2+}$-activated $K^+$ channel: variation of the length of the alkylene chain. *J. Med. Chem.* 1996, 39, 3592–3595.
[11] Qin, D.; Byun, H.-S.; Bittman, R. Palmitic and palmitoleic acids from THF-$d_8$. *J. Org. Chem.* 1996, 61, 8709–8711.
[12] Supporting Information Available: Synthetic methods are detailed along with a listing of NMR spectra and HPLC chromatograms of key new compounds. See any current masthead page of Molecular Pharmacology for ordering and Internet access instructions.
[13] Qin, D.; Sullivan, R. M.; Berkowitz, W. F.; Bittman, R.; Rotenberg, S. A. Inhibition of protein kinase C$\alpha$ by dequalinium analogues: dependence on linker length and geometry. *J. Med. Chem.* 2000, 43, 1413–1417.
[14] Taylor, E. P. Synthetic neuromuscular blocking agents. Part I. Heterocyclic decamethylene bis (quaternary ammonium salts). *J. Chem. Soc.* (Lond.) 1951, pp. 1150–1157.
[15] House, C.; Kemp, B. E. Protein kinase C contains a pseudosubstrate prototope in its regulatory domain. *Science* 1987, 238, 1726–1728.
[16] Kampfer, S.; Hellbert, K.; Villunger, A.; Doppler, W.; Baier, G.; Grunicke, H. H.; Uberall, F. Transcriptional activation of c-fos by oncogenic Ha-Ras in mouse mammary epithelial cells requires the combined activities of PKC-lambda, epsilon and zeta. *EMBO J.* 1998, 17, 4046–4055.

What is claimed is:

1. A composition for protecting human skin from harmful effects of the sun, the composition comprising a topically effective amount of:

(a) a first chemical compound that absorbs ultraviolet light sufficiently to reduce significantly the damage to human skin from harmful effects of ultraviolet light; and (b) a second chemical compound having the formula:

$$(Q\text{-}L\text{-}Q)_w^{+2}X_y^{-z}$$

wherein:

Q represents 4-E-2-$R_3$-1-quinolinium;

E represents $NR_1R_2$, COO $R_1$, $OR_1$, I, Br, Cl, F, or $NO_3$

N represents a nitrogen atom;

$R_1$ and $R_2$ independently represent hydrogen or lower alkyl;

$R_3$ represents E, hydrogen or lower alkyl;

L represents a chain comprising n atoms, the atoms in the chain being t carbon atoms and 0 to approximately 0.5t heteroatoms;

the minimum value of n is 12;

the maximum value of n is 22;

X represents an anion; and w represents 1 or 3, y represents 1 or 2 and z represent 1, 2 or 3, with the proviso that 2w=yz.

2. The composition of claim 1 wherein the second compound has the formula:

$$(Q\text{-}L\text{-}Q)^{+2}X_y^{-z}$$

wherein:

Q represents 4-$NR_1R_2$-2-$R_3$-1-quinolinium;

N represents a nitrogen atom;

$R_1$ and $R_2$ independently represent hydrogen or lower alkyl;

$R_3$ represents hydrogen or lower alkyl;

L represents a 1,n-aliphatic chain comprising n carbon atoms;

n represents 12–22;

X represents an anion; and y and z represent 1 or 2 with the proviso that yz=2.

3. The composition of claim 1 wherein E represents $NR_1R_2$.

4. The composition of claim 1 wherein $R_3$ represents hydrogen or lower alkyl.

5. The composition of claim 1 wherein E represents $NR_1R_2$ and $R_3$ represents hydrogen or lower alkyl.

6. The composition of claim 1 wherein the heteroatoms are oxygen, sulfur, or nitrogen atoms.

7. The composition of claim 6 wherein L comprises at least one unit of ethylene glycol.

8. The composition of claim 6 wherein L comprises at least one unit of ethylenediamine.

9. The composition of claim 1 wherein L represents a saturated aliphatic chain.

10. The composition of claim 1 wherein L represents an unsaturated aliphatic chain.

11. The composition of claim 10 wherein the unsaturated aliphatic chain comprises at least one double bond.

12. The composition of claim 11 wherein the at least one double bond is a trans double bond.

13. The composition of claim 10 wherein the unsaturated aliphatic chain comprises at least one triple bond.

14. The composition of claim 1 wherein n represents 12–16.

15. The composition of claim 1 wherein n represents 14–16.

16. The composition of claim 1 wherein n represents 14.

17. The composition of claim 1 wherein y represents 2.

18. The composition of claim 17 wherein X represents a halide.

19. The composition of claim 17 wherein X represents iodide.

20. The composition of claim 1 wherein $R_1$ and $R_2$ represent a hydrogen atom.

21. The composition of claim 1 wherein $R_3$ represent a methyl group.

22. The composition of claim 1 wherein $(Q\text{-}L\text{-}Q)^{+2}$ represents 1,1'-(1,14-tetradecanediyl)-bis(4-amino-2-methylquinolinium).

23. The composition of claim 22 wherein $X_y^{-z}$ represents diiodide.

* * * * *

UNITED STATES PATENT AND TRADEMARK OFFICE
CERTIFICATE OF CORRECTION

PATENT NO. : 6,790,962 B1
DATED : September 14, 2004
INVENTOR(S) : Rotenberg et al.

It is certified that error appears in the above-identified patent and that said Letters Patent is hereby corrected as shown below:

Column 3,
Line 24, "intracellular PKC" should read -- intracellular $PKC_\alpha$ --.

Column 12,
Line 38, "with PKC," should read -- with $PKC_\alpha$, --.
Line 51, "of PKC," should read -- of $PKC_\alpha$, --.

Column 14,
Line 41, "for $C_{30}H_{38}N_{412}$:" should read -- for $C_{30}H_{38}N_4I_2$: --.

Column 15,
Line 32, "Total PKC," should read -- Total $PKC_\alpha$, --.
Line 57, "(1200 $UV/cm^2$)" should read -- (1200 $\mu W/cm^2$) --.

Column 17,
Line 20, "as previously described PKC catalytic" should read -- as previously described$^2$. PKC catalytic --.
Line 54, "RACK-I" should read -- RACK-1 --.

Column 18,
Line 10, "kinase C" should read -- kinase $C_\alpha$ --.

Column 20,
Line 28, "$(Q-L-Q)^{+2}$" should read -- $(Q-L-Q)_w^{+2}$ --.

Signed and Sealed this

Eighteenth Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,790,962 B1 | Page 1 of 2 |
| APPLICATION NO. | : 10/328693 | |
| DATED | : September 14, 2004 | |
| INVENTOR(S) | : Rotenberg et al. | |

It is certified that error appears in the above-identified patent and that said Letters Patent is hereby corrected as shown below:

<u>Title page,</u>
Item [75], Inventor, delete "A. David Baker".

<u>Column 3,</u>
Line 24, now reads "intracellular PKC" should read -- intracellular $PKC_\alpha$ --.

<u>Column 12,</u>
Lines 38 and 51, now reads "with PKC," should read -- with $PKC_\alpha$, --.

<u>Column 14,</u>
Line 41, now reads "for $C_{30}H_{38}N_{412}$:" should read -- for $C_{30}H_{38}N_4I_2$: --.

<u>Column 15,</u>
Line 32, now reads "Total PKC," should read -- Total $PKC_\alpha$, --.
Line 57, now reads "(1200 $UV/cm^2$)" should read -- (1200 $\mu W/cm^2$) --.

<u>Column 17,</u>
Line 20, now reads "as previously described PKC catalytic" should read -- as previously described[2]. PKC catalytic --.
Line 54, now reads "RACK-I" should read -- RACK-1 --.

<u>Column 18,</u>
Line 10, now reads "kinase C" should read -- kinase $C_\alpha$ --.

UNITED STATES PATENT AND TRADEMARK OFFICE
CERTIFICATE OF CORRECTION

PATENT NO. : 6,790,962 B1  
APPLICATION NO. : 10/328693  
DATED : September 14, 2004  
INVENTOR(S) : Rotenberg et al.

It is certified that error appears in the above-identified patent and that said Letters Patent is hereby corrected as shown below:

Column 20,  
Line 28, now reads "$(Q-L-Q)^{+2}$" should read -- $(Q-L-Q)_w^{+2}$ --.

Signed and Sealed this

Twenty-seventh Day of June, 2006

JON W. DUDAS  
*Director of the United States Patent and Trademark Office*